United States Patent
Bransky et al.

(10) Patent No.: US 9,683,984 B2
(45) Date of Patent: Jun. 20, 2017

(54) OPTICAL IMAGING BASED ON VISCOELASTIC FOCUSING

(71) Applicants: Avishay Bransky, Kyriat Tivon (IL); Max Herzberg, Sitrya (IL)

(72) Inventors: Avishay Bransky, Kyriat Tivon (IL); Max Herzberg, Sitrya (IL)

(73) Assignee: Pixcell Medical Technologies Ltd., Yokneam Ilit (IL)

(*) Notice: Subject to any disclaimer, the term of this patent is extended or adjusted under 35 U.S.C. 154(b) by 493 days.

(21) Appl. No.: 14/330,062

(22) Filed: Jul. 14, 2014

(65) Prior Publication Data

US 2014/0322801 A1  Oct. 30, 2014

Related U.S. Application Data

(63) Continuation of application No. 13/122,299, filed as application No. PCT/IL2009/000945 on Oct. 1, 2009, now Pat. No. 9,494,570.

(60) Provisional application No. 61/102,015, filed on Oct. 2, 2008.

(51) Int. Cl.
| | |
|---|---|
| *C12M 1/34* | (2006.01) |
| *G01N 33/49* | (2006.01) |
| *G01N 15/14* | (2006.01) |
| *B01L 3/00* | (2006.01) |
| *B01F 13/00* | (2006.01) |
| *F21V 8/00* | (2006.01) |

(52) U.S. Cl.
CPC ..... *G01N 33/4915* (2013.01); *B01F 13/0064* (2013.01); *B01L 3/502761* (2013.01); *B01L 3/502776* (2013.01); *G01N 15/1404* (2013.01); *G01N 15/147* (2013.01); *G01N 15/1475* (2013.01); *G01N 15/1484* (2013.01); *B01L 2200/0636* (2013.01); *B01L 2200/0647* (2013.01); *B01L 2300/0867* (2013.01); *G01N 2015/1497* (2013.01); *G02B 6/0021* (2013.01); *G02B 6/0038* (2013.01)

(58) Field of Classification Search
CPC .................................................. C12M 1/3446
See application file for complete search history.

(56) References Cited

U.S. PATENT DOCUMENTS

| | | |
|---|---|---|
| 4,400,370 A | 8/1983 | Kass |
| 4,581,223 A | 4/1986 | Kass |
| 5,799,682 A | 9/1998 | Affleck et al. |
| 6,097,485 A | 8/2000 | Lievan |
| 6,862,092 B1 | 3/2005 | Ibsen et al. |

(Continued)

FOREIGN PATENT DOCUMENTS

WO   WO 2008/149365   12/2008

OTHER PUBLICATIONS

Extended European Search Report dated Nov. 13, 2014 for European Application No. 14177083.4 (9 pages).
Extended European Search Report dated Nov. 13, 2014 for European Application No. 09817362.8 (10 pages).
Bransky et al., "Correlation between erythrocytes deformability and size: A study using a microchannel based cell analyzer," Microvascular Research, Academic Press, US, vol. 73, No. 1, Jan. 12, 2007 (7 pages).

(Continued)

*Primary Examiner* — Rosanne Kosson
(74) *Attorney, Agent, or Firm* — Finnegan, Henderson, Farabow, Garrett & Dunner, LLP

(57) ABSTRACT

An apparatus arranged for examining particles, comprising: a cartridge having at least one microchannel, a viscoelastic fluid flowing in the microchannel, the fluid comprising a suspension of particles, thereby effecting alignment of the particles in at least one-dimensional array parallel to the fluid flow, and an optical magnifying means generating an image of the particles in the microchannel.

14 Claims, 8 Drawing Sheets

(56) References Cited

U.S. PATENT DOCUMENTS

| | | |
|---|---|---|
| 6,959,618 B1 | 11/2005 | Larsen |
| 7,312,085 B2 | 12/2007 | Chou et al. |
| 7,843,563 B2 | 11/2010 | Fritz et al. |
| 2003/0127609 A1 | 7/2003 | El-Hage et al. |
| 2004/0043506 A1 | 3/2004 | Haussecker et al. |
| 2004/0070757 A1 | 4/2004 | Moore et al. |
| 2005/0255458 A1 | 11/2005 | Polansky |
| 2005/0271548 A1 | 12/2005 | Yang et al. |
| 2007/0190525 A1 | 8/2007 | Gu et al. |
| 2007/0207061 A1 | 9/2007 | Yang et al. |
| 2007/0258889 A1 | 11/2007 | Douglas et al. |
| 2008/0030732 A1 | 2/2008 | Yaroslavsky et al. |
| 2010/0178666 A1 | 7/2010 | Leshansky et al. |

OTHER PUBLICATIONS

Bransky, Avishay et al., (2007) The rheologic properties of erythrocytes: a study using an automated rheoscope. Rheol Acta 46(5):621-627.

Huang, P.Y. et al., (1997) Direct simulation of the sedimentation of elliptic particles in oldroyd-B fluids. URL://www.aem.umn.edu/people/faculty/josephy/archieve/docs/ellipse.pdf.

Leshansky, A.M. et al., (2007) Turnable Nonlinear Viscoelastic "Focusing" in a Microfluidic Device Phys. Rev. Lett. 98(23):234501 Epub Jun. 7, 2007.

International Search Report and Written Opinion of PCT/IL09/000945 dated Feb. 5, 2010 (11 pages).

Chinese Third Office Action for Chinese Application No. 2014103120857, dated Jan. 24, 2017.

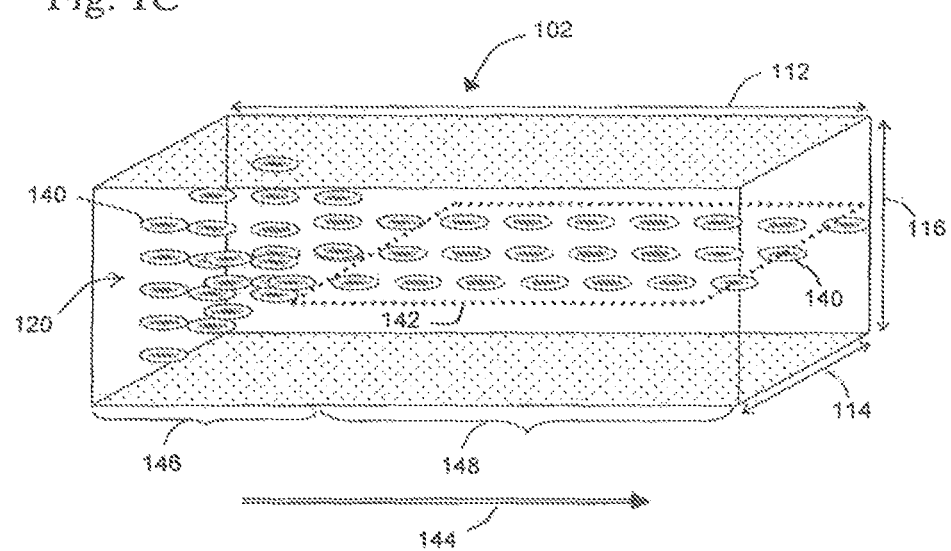

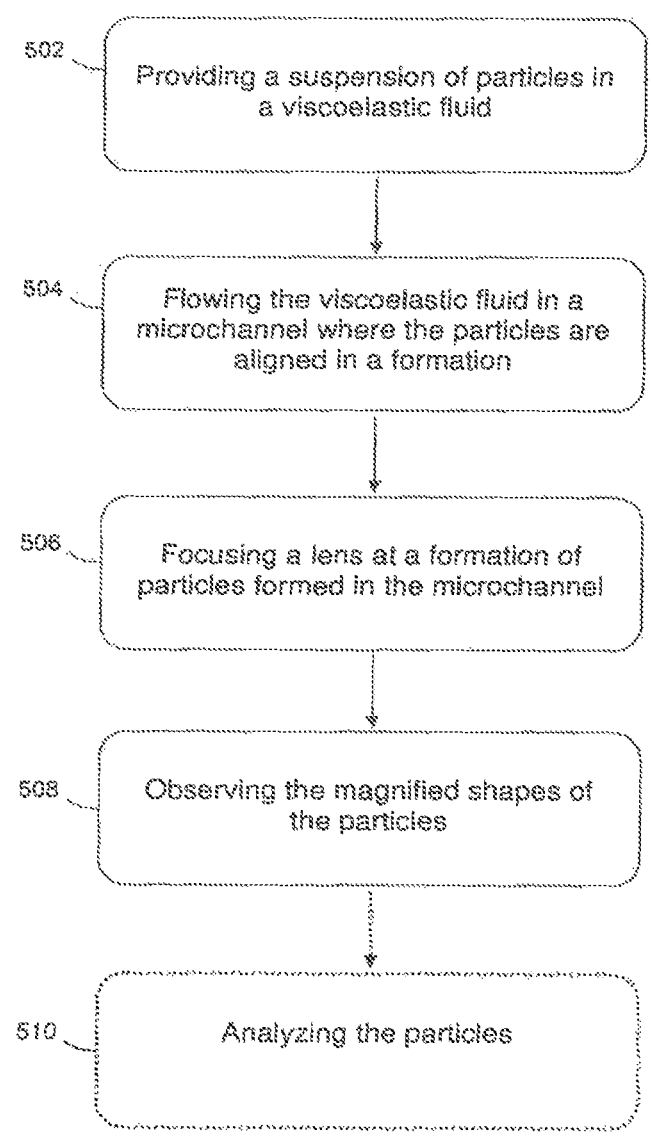

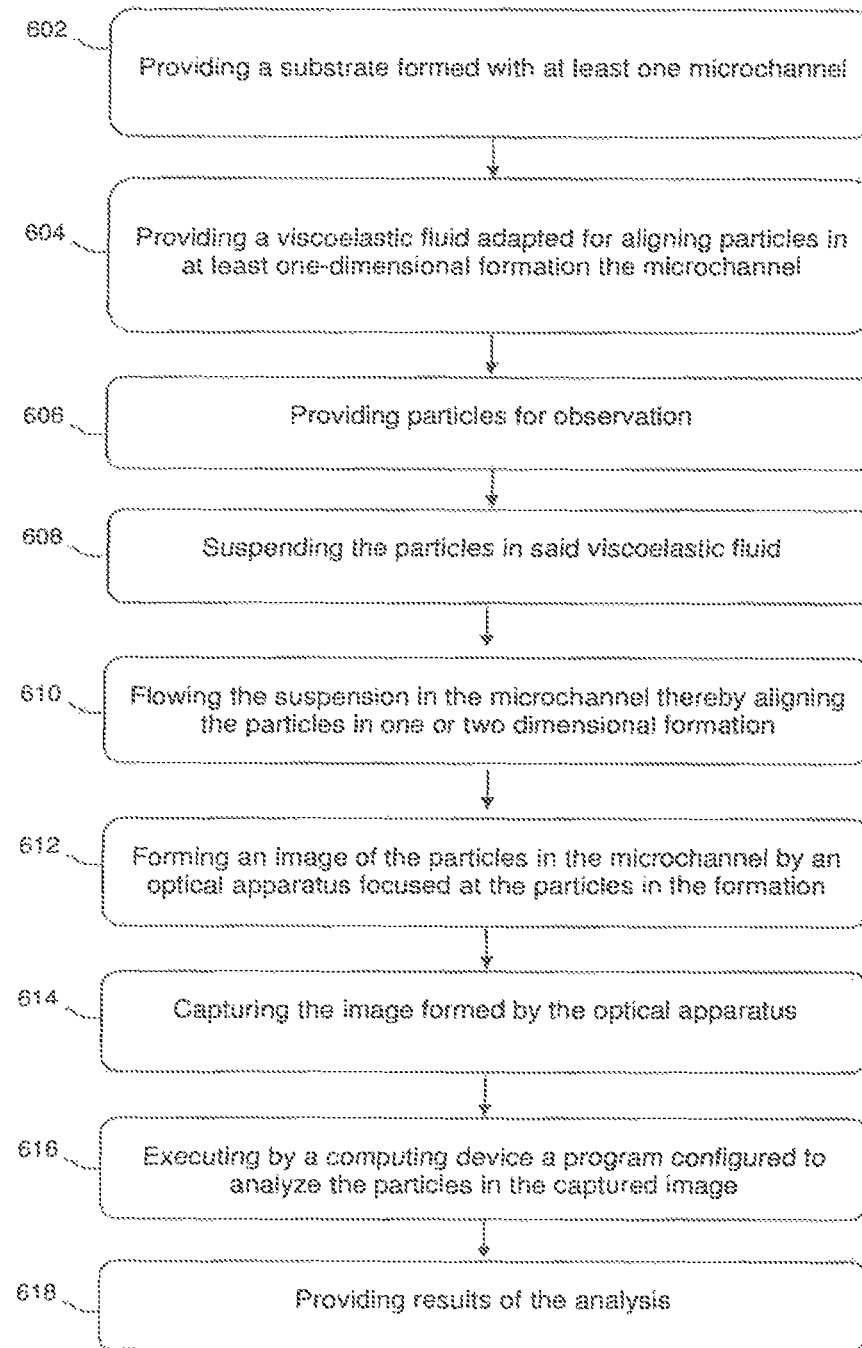

OPTICAL IMAGING BASED ON VISCOELASTIC FOCUSING

This application is a continuation of application Ser. No. 13/122,299, filed Oct. 26, 2011, which is a U.S. National Phase Application of International Application No. PCT/IL09/00945, filed Oct. 1, 2009, which claims the priority of U.S. Provisional Application No. 61/102,015, filed Oct. 2, 2008, all of which are incorporated herein by reference.

FIELD OF THE INVENTION

The invention relates generally to microfluidic devices, and in particular the invention relates to apparatus and methods for magnifying images of particles aligned in a microfluidic device.

BACKGROUND OF THE INVENTION

The microfluidics technology is typically identified by employing devices having one or more channels with at least one dimension less than 1 millimeter and minute amounts of fluids, typically in the order of nano- and pico-liters.

Microfluidics is used in various fields, such as chemical and biological reactions and analysis or ink-jet nozzles fabrication.

Microfluidics technologies enable to develop small, cost effective and efficient systems, such as a lab-on-a-chip where entire complex chemical management and analysis systems can be created in a microfluidic chip and interfaced with, for example, electronics and optical detection systems.

Applying microfluidics to visualize microscopic objects was disclosed for example, in US applications 2005/0271548 or 2007/207061 to Yang et al., and a blood cytometer was described, for example, in U.S. Pat. No. 6,097,485 to Lievan or U.S. Pat. No. 6,959,618 to Larsen. U.S. Pat. No. 7,312,085 to Hou-Pu et al. discloses apparatus, methods and kits for microfluidic manipulation and/or detection of particles such as cells and/or beads.

An apparatus and methods using a fluid having viscoelastic properties such that infusing a fluidic suspension of particles in a microchannel increases the concentration of the particles in a focus region inside the microchannel ('viscoelastic focusing') is disclosed in A. M. Leshansky, A. Bransky, N. Korin, and U. Dinnar, *Tunable Nonlinear Viscoelastic "Focusing" in a Microfluidic Device*, Phys. Rev. Lett. 98, 234501 (2007) and in PCT application WO2008/149365 of which a co-inventor (Bransky) is the inventor of the present invention.

SUMMARY OF THE INVENTION

An aspect of some embodiments of the invention relates to a method and apparatus for optical imaging of particles suspended in a viscoelastic fluid flowing in a microchannel such that the particles are aligned in at least one-dimensional array parallel to the fluid flow.

In some embodiments of the invention, one or more microchannels are formed on a generally planar substrate, such as a plastic or glass plate. The particles suspended in a viscoelastic fluid that flows in a microchannel align in a one-dimensional or two-dimensional array in the microchannel. An optical objective lens focused at the array provides a magnified image of the particles, optionally under a suitable illumination. The image may be captured by an image acquisition apparatus and subsequently analyzed, manually and/or by computerized programs.

In some embodiments of the invention, a substrate, with a microchannel and optionally other structures (hereinafter also a 'cartridge') is removably placed in an apparatus for acquiring and analyzing the particles image, providing designated results (hereinafter, a 'reader'). Preferably the reader is compactly built, optionally as a portable device.

In some embodiments of the invention, the cartridge comprises the required structures and/or mechanisms and/or materials to produce the aligned flow of suspended particles. Optionally or alternatively, some of the structures and/or mechanisms and/or materials are provided in the reader or by auxiliary accessories.

Preferably the cartridge is disposable, and preferably produced economically from inexpensive materials and/or by a cost effective process such as a continuous mass production process.

It should be emphasized that the viscoelastic focusing, namely, the alignment of particles in an orderly array in the viscoelastic flow in a microchannel is a key factor in obtaining a sharp optically focused image. Furthermore, depending on the structure and rigidity (or flexibility or pliability) of the particles and the effect of the shear flow in the viscoelastic fluid flow the particles may deform and align in some favored orientation. For example, red blood cells, normally having a biconcave shape, are elongated in the flow direction and aligned with the flat side up and down, enabling to capture a sharp focused image of consistent cell shapes rather than cells with various orientation, parts of which are out of focus. It should be also noted that viscoelastic flow and focusing can be intrinsically obtained merely under pressure gradient without any external field (e.g. electric or magnetic field), simplifying the apparatus and method used with viscoelastic focusing.

In the specification and claims the following terms and derivatives thereof imply the respective non-limiting characterizations:

A microchannel—a channel such as a groove or tube having a length of at least about or larger than 100 μm and a rounded or rectangular cross section perpendicular to the length where at least one dimension thereof is about or smaller than 100 μm.

A shallow microchannel—a microchannel having, with relation to an underlying surface, a horizontal cross sectional dimension ('width') significantly larger than the vertical dimension ('height'), for example, by a factor of five or more.

Particles—microscopic particles. Typically particles having a mean largest dimension of about or less then 25 μm or an average diameter of about or less than 15 μm. The particles may be of organic or inorganic origin, or a combination thereof, including microspheres, microbeads, minerals (e.g. clay), pollen, micelles, vesicles, organelles or cells (either of a multicellular organism or single cell such as a bacterium), as well as living cells.

Suspended (particles)—particles dispersed throughout a fluid such as in a suspension, not excluding an emulsion (e.g. fatty particles in a hydrophilic fluid).

A microstructure—structured having at least one dimension in the sub-millimeter region, typically 100 μm or less (e.g. a microchannel or inlet and outlet thereof, see below).

Substrate—a generally planar material, such as a plastic or glass plate, suitable for forming structures therein and/or thereon.

Cartridge—a substrate formed with one or more microchannels and optional other microstructures and optionally comprising additional one or more elements and/or mechanisms.

Objective—an optical magnification apparatus or system comprising, for example, one or more lenses and/or mirrors and/or prisms, adapted or designed for manual viewing and/or for electronic acquisition.

Bandwidth (of wavelength)—the width at half the maximal height of a light spectrum curve.

Monochromatic (light)—Having or appearing to have only one color, characterized by a narrow bandwidth such as lower than 100 nm or 50 nm.

A compact apparatus—an apparatus comprising components closely or densely packed to reduce size and/or weight, possibly on the expense of price and/or performance.

Generally planar—having a mostly a planar surface, not excluding some deviations therefrom, such as curvatures or dents or humps. Generally may apply similarly to other characteristics such as generally columnar.

Semi-—partly, or imperfectly, or to some degree of an entity, such as, without limiting, in a region between 25% and 75% of as entity.

Translucent—semi-transparent and/or diffusive (scattering transmitted and reflected light).

Biological (compounds, material)—a compound or material derived from a biological source or is active or participates in a biological process or has a similar structure to biological compound as characterized.

Solid state (light source)—electronic (rather than electrical) device emitting light without aid of a filament or gas discharge and which typically smaller than the latter two. For example, LED, OLED, PLED or other devices based on electro-luminescence or thermo-luminescence (stimulated by the application of heat, to temperatures below those that result in incandescence) or chemiluminescence.

According to an aspect of some embodiments of the present invention there is provided an apparatus arranged for examining particles, comprising:

(a) a cartridge having at least one microchannel;
(b) a viscoelastic fluid flowing in the microchannel, the fluid comprising a suspension of particles, thereby effecting alignment of the particles in an at least one-dimensional array parallel to the fluid flow; and
(c) an optical magnifying objective generating an image of the particles in the microchannel.

In some embodiments, the apparatus farther comprises a holder configured to releasably grip the cartridge.

In some embodiments of the invention, the cartridge is disposable.

In some embodiments of the invention, the cartridge is routinely replaceable.

In some embodiments, the cartridge further comprises at least one microstructure facilitating the flow of the viscoelastic fluid in the microchannel.

In some embodiments, the flow of the viscoelastic fluid in the microchannel is driven, at least partially, by a pressure gradient.

In some embodiments, the flow of the viscoelastic fluid in the microchannel is Independent of any one of externally applied electric or magnetic or centrifugal or gravitational force.

In some embodiments, the at least one-dimensional array is a two-dimensional generally planar array.

In some embodiments, the particles are halted in an array in the microchannel.

In some embodiments, the apparatus further comprises at least one light source illuminating the particles in the microchannel.

In some embodiments, the light is monochromatic.

In some embodiments, the light source distance from the cartridge is minimized at least optically or mechanically or as a combination thereof.

In some embodiments, the at least one light source is at least connected to or comprised in the cartridge.

In some embodiments, the light source comprises a solid-state light source.

In some embodiments, the objective is structured to veduce at least one of complexity, cost, size, or a combination thereof at the expense of least one of a chromatic aberration correction or depth of field.

In some embodiments, the objective is fixedly focused at the particles array in the microchannel.

In some embodiments, the objective comprises at least one plastic optical element.

In some embodiments, the viscoelastic fluid comprises a solvent and ingredients providing sufficient viscosity and elasticity for alignment of suspended particles in the fluid flowing in the microchannel.

In some embodiments, the ingredients comprise polymers having molecular weight between about 50 kDa and 1000 kDa.

In some embodiments, the viscoelastic fluid comprises at least one ingredient for dispersing the suspended particles.

In some embodiments, the viscoelastic fluid is biocompatible.

In some embodiments, the particles are acquired from a biological sample.

In some embodiments, the biological sample comprises at least one of a blood, plasma, lymph, urine, cerebrospinal fluid (CSF) or bone marrow.

In some embodiments, the particles comprise cells.
In some embodiments, the cells comprise blood cells.
In some embodiments, the cells comprise bacteria.
In some embodiments, the cells comprise living cells.
In some embodiments, the particles comprise compounds or macromolecules that react with or bind, to other compounds or macromolecules present on the particles.

In some embodiments, the bound compounds comprise biological compounds.

In some embodiments, the bound compounds comprise at least one of a protein or DNA or RNA.

In some embodiments, the bound compounds comprise at least one of an antigen or antibody.

In some embodiments, the other compounds present on the particles comprise biological compounds.

In some embodiments, the particles comprise a magnetic constituent.

In some embodiments, the magnetic constituent comprises a magnetic core.

In some embodiments, the particles comprise a ferromagnetic constituent.

In some embodiments of the invention, the apparatus further comprises an apparatus for electronically capturing the image generated by the objective.

In some embodiments of the invention, the apparatus further comprises at least one processor executing a program configured for analyzing particles in the captured image and providing at least one of a qualitative or a quantitative result.

In some embodiments, the results comprise at least one of shape of particles, type of particles, indication of a physiological condition or indication of a pathological condition.

In some embodiments, the results comprise at least one of particle count, particle concentration, particle size, particle size distribution, particle shape, or a derivation thereof.

In some embodiments, the results comprise determination of a cell type. In further embodiments for the cell type the results comprise at least one of cells count, cell concentration, cell size, cell size distribution, cell shape, cel morphology, or a derivation thereof.

In some embodiments, the results comprise at least one routine clinical test result.

In some embodiments, the results comprise at least one routine clinical blood test result.

In some embodiments, the results comprise at least one of a value or an indication of at least one of biological or clinical significance.

In some embodiments, the results comprise at least one of a value or an indication of meningitis.

In some embodiments, the results comprise at least one of a value or an indication of leukemia.

In some embodiments, the results comprise at least one of a value or an indication of bacterial infection.

In some embodiments, the results comprise at least one of a value or an indication of fetal lung maturity.

In some embodiments, providing results comprises at least one of storing the results on a machine-readable medium, displaying the results or printing the results.

In some embodiments of the invention, the apparatus further comprises a display screen.

In some embodiments, the apparatus further comprises a printer.

According to an aspect of some embodiments of the present invention there is provided a kit for examining particles, comprising at least one cartridge formed with at least one microchannel suitable for aligning particles suspended in a viscoelastic fluid flowing therein in at least one-dimensional array parallel to the flow In some embodiments, a cartridge further comprises microstructures facilitating flowing the viscoelastic fluid in said microchannel.

In some embodiments, the cartridge comprises at least one of the viscoelastic fluid or a constituent thereof.

In some embodiments of the invention, the kit comprises at least one of the viscoelastic fluid or a constituent thereof.

In some embodiments, the kit comprises an apparatus for at least one of observing a magnified image of the particles or analyzing the particles.

In some embodiments, the cartridge is compatible with a microscope slide.

In some embodiments, the kit comprises an operation guide.

According to an aspect of some embodiments of the present invention there is provided a method for analyzing particles, comprising:

(a) providing a substrate formed with at least one microchannel;

(b) providing a viscoelastic fluid suitable for flowing a suspension of particles in the microchannel thereby aligning the particles in at least one-dimensional array parallel to the flow, (c) providing particles for analysis;

(d) suspending the particles in said viscoelastic fluid;

(e) flowing the viscoelastic fluid with the suspended particles in said microchannel such that the particles align in at least one-dimensional array parallel to the fluid flow; and (f) generating an image of the particles in the microchannel by an optical apparatus focused at the particles in said array.

In some embodiments of the invention, the method further comprises analyzing the image.

In some embodiments of the invention, analyzing comprises:

(a) capturing the image generated by the optical apparatus; and (b) executing by a computing device a program configured to analyze particles in the captured image.

In some embodiments, analyzing further comprises providing at least one of a qualitative or quantitative result of the analysis.

In some embodiments, providing results comprises at least one of storing the results on a machine-readable medium or displaying the results or printing the results.

In some embodiments, the particles comprise cells.

In some embodiments, the particles comprise living cells.

In some embodiments, the particles comprise blood cells.

In some embodiments, the particles comprise compounds that react with or attach to other compounds.

In some embodiments, flowing the viscoelastic fluid in the microchannel comprises applying a pressure gradient.

In some embodiments, flowing the viscoelastic fluid is independent of any one of externally applied electric or magnetic or centrifugal or gravitational force.

In some embodiments of the invention, the at least one-dimensional array is a two-dimensional generally planar array.

In some embodiments, providing a viscoelastic fluid comprises dissolving in a solvent ingredients providing the fluid with sufficient viscosity and elasticity for aligning particles in the microchannel.

BRIEF DESCRIPTION OF THE DRAWINGS

In the drawings, identical or duplicate or equivalent or similar structures, elements, or parts that appear in more than one drawing are generally labeled with the same reference numeral, optionally with an additional letter or letters for reference to particular objects. Duplicate or equivalent or similar parts may not be repeatedly labeled and/or described. Dimensions of components and features shown in the figures are chosen for convenience or clarity of presentation and are not necessarily shown to scale or true perspective, for convenience of clarity, some elements or structures are not shown or shown only partially and/or with different perspective.

FIG. 1C schematically illustrates a perspective view of a section of microchannel with suspended particles flowing therein, according to exemplary embodiments of the invention;

FIG. 5 schematically illustrates a flowchart outlining actions in observing a magnified image of particles aligned in viscoelastic fluid, according to exemplary embodiments of the invention;

FIG. 6 schematically illustrates a flowchart of actions for capturing and analyzing a magnified image of particles aligned in viscoelastic fluid, according to exemplary embodiments of the invention;

DESCRIPTION OF EMBODIMENTS OF THE INVENTION

Figure 1A:
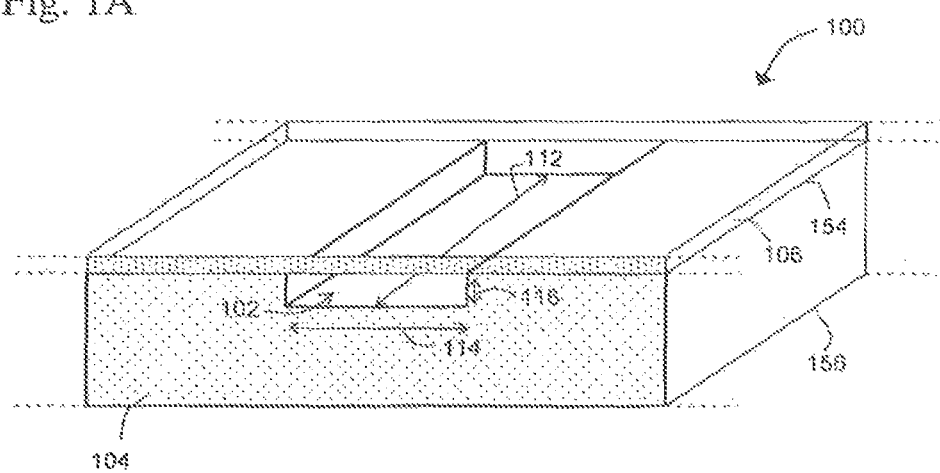
FIG. 1A schematically illustrates a perspective partial view of a cartridge with a covered microchannel formed on a substrate, according to exemplary embodiments of the invention.

The following description relates to one or more non-limiting examples of embodiments of the invention. The invention is not limited by the described embodiments or drawings, and may be practiced in various manners or configurations or variations. The terminology used herein should not be understood as limiting unless otherwise specified.

The non-limiting section headings used herein are intended for convenience only and should not be construed as limiting the scope of the invention.

General Terminology

Without limiting, in the specifications and claims, unless otherwise specified, the terms 'processor' or 'computer' or derivatives thereof denote an apparatus that is capable of carrying out a provided or an incorporated program and/or is capable to controlling and/or accessing data storage apparatus and/or other apparatus such as input and output ports.

Without limiting, in the specifications and claims, unless otherwise specified, the terms 'software', 'program', 'procedure' or 'software module' ('module') or 'software code' ('code') may be used interchangeably and denote one or more instructions or directives accessible and executable by an apparatus such as a processor, optionally involving other hardware or software components such as memory, input/output interface or operating system.

In the specification and claims, unless otherwise specified, the terms 'preferred', 'preferably', 'typical' or 'typically' and their inflections and conjugates do not limit the scope of the invention or embodiments thereof.

In the specification and claims, unless otherwise specified, the terms 'comprises', 'comprising', 'includes', 'including', 'having' and their inflections and conjugates denote 'including but not limited to'.

When a range of values is recited, it is merely for convenience or brevity and includes all the possible subranges as well as individual numerical values within that range. Any numeric value, unless otherwise specified, includes also practical close values enabling an embodiment or a method, and integral values do not exclude fractional values.

Overview

In a typical embodiment, a viscoelastic fluid is mixed with particles forming a suspension and flowed into a microchannel formed in a cartridge where the particles align in the fluid flow in a generally columnar or planar array. The cartridge is placed in a reader where the microchannel is optionally illuminated and a lens focused at the particles array magnifies the particles image. The magnified image is acquired by a camera that transfers the image to a computer that processes and analyzes the image to provide some designated results.

The concise description above is intended, without limiting, to provide a framework and/or reference to a more elaborate description and discussion of variants of some embodiments of the invention below.

Viscoelastic Fluid

In some embodiments of the invention, the viscoelastic fluid comprises a medium (e.g. a solvent) such as water and additional compositions or substances that provide a sufficiently high viscosity (e.g. >5 cP) and elasticity for aligning particles in a microchannel, for example, polyacryiamide (PAA) which enhances elasticity of solutions.

In some embodiments, the medium comprises dissolved high molecular weight (MW) polymers (e.g. 50-1000 kDa), such as polyacryiamide (PAA) as above, polyethyleneglycol (PEG), polysucrose, polyglucose (Dextran), methyicelMose or xanthan gum. Using biocompatible substances may be advantageous when the particles comprise biological entities or molecules, such as living cells or beads coated or linked with antibodies.

In some cases the high molecular weight polymers induce aggregation of particles such as living cells (see, for example, FIG. 8), and may have other detrimental effects on the behavior of the particles (such as the motion of the membrane of red blood cells, see below). To alleviate or reduce or eliminate the detrimental effects, counter measures may be used such as one or more of: (a) adding low MW polymers to the high MW, (b) adding Urea and/or Lecithin and/or aspirin (acetylsalicylic acid), (c) using polymers with a wide MW distribution or (d) Poloxamers (polymer surfactants).

Furthermore, adding sphering agents to the high molecular weight polymers causes cells such as red blood cells to acquire a spherical shape rather than the normal bi-concave disc shape, stomatocyte, echincocyte or other shapes. Sphering is advantageous in several respects. First by significantly reducing aggregation of cells which is induced by the high molecular weight polymers used for viscoelastic focusing. Second spherical shapes are more efficiently focused by the viscoelastic forces. And third, having spherically shaped cells enables better optical focusing (relative to other shapes) and facilitates more convenient and/or more reliable geometrical derivations such as diameter or volume of the cells (relative to other shapes such as flattened or elongated discs). Several sphering agents are used in cytometry for reducing cell orientation noise from scattering, for example, alkali metal salt of an alkyl sulfate (e.g. sodium dodecyl sulfate), or zwitterionic surfactant (e.g. 3-(dodecyldimethylammonio) propanesulfonate (DAPS) or N30 tetradecyl-N, N-dimethyl-3-ammonio-1-propanesulfonate (TDAPS)), or Nonionic surfactants (e.g. octyl phenol ethoxylate).

In some cases, high MW polymers include Dextran>50 kDa, PVP>50 kDa, methyl cellulose, Alginate, Ficoll or PAA where, in some cases, low MW include Dextran<40 kDa, PEG<40 kDa or PAA.

Cartridge

In typical embodiments of the invention, the cartridge is fabricated by forming one or more microchannels on a substrate, optionally forming additional structures or mechanisms, such as structures for fluid entrance and exit in and out of the microchannel (inlet and outlet, respectively), a pressure gradient mechanism, materials mixing chamber or a pressure valve (hereinafter collectively denoted as 'microstructures'). Optionally, the substrate is formed with a structure and/or mechanism for holding and/or placing the cartridge in a reader or another apparatus.

In the following description, referring to a microchannel or another microstructure implies, without limiting, a plurality of such structures.

In typical embodiments, the substrate is a generally planar piece of a transparent material having a length and a width in the order of magnitude of a centimeter and a thickness in the order of magnitude of a millimeter, in some cases resembling a microscope slide or slide cover. The substrate is made of materials such as PMMA (polymethylmethacrylate), PDMA (polydimethylsiloxane) or other polymeric materials or silicon or glasses in which microstructures, including biocompatible microstructures, can be fabricated. In some cases the fabrication includes using one or more of several high throughput methods, such as injection molding, soft lithography, laser ablation, X-ray photolithography, fiber drawing or hot embossing.

In some cases, the microchannel and/or other microstructures and/or the cartridge (or a part thereof) are capped with a layer of material such as by bonding in high temperature and pressure, or by using a suitable adhesive. Optionally, the cartridge in coated with a protective layer (e.g. scratch resistant) and is optionally placed in a protective and/or operative case (e.g. holes or grooves for placing in a reader). Typically the cover and/or coating are transparent, at least for tire light bandwidth used for viewing the microchannel and contents thereof.

In some embodiments, the microstructures are fabricated by following methods known in the art, such as in *Introduction to Microfabrication* by S. Franssila, John Wiley and Sons, 2004 ISBN 0470851058, 9780470851050 or in other publication such as *Printing meets lithography, The Industrial Physicist*, 8(4) 2002, or A. Bransky et al., *Biosens. Bioelectron.* 22, 165 (2006) and A. Bransky et al., *Microvasc. Res.* 73, (2007). Other references include, for example, R. M. McCormick, R. J. Nelson, M. G. Alonso-Amigo, D. J. Benvegnu and H. H. Hooper, *Anal. Chem.,* 1997, 69, 2626, D. Qin, Y. Xia and G. M. Whitesides, *Adv. Mater.,* 1996, 8, 917, F. Dang, S. Tabata, M. Kurokawa, A. A. Ewis, L. Zhang, Y. Yamaoka, S. Shinohara, Y. Sinohara, M. Ishikawa and Y. Baba, *Anal. Chem.,* 2005, 77, 2140, Z. Meng, S Qi, S. A Soper and P. A. Limbach, *Anal. Chem.,* 2001, 73, 1286, Z. Chen, Y. Gao, J. Lin, R. Su and Y. Xie, *J. Chromatogr., A,* 2004, 1038, 239, L. Martynova, L. E. Locascio, M. Gaitan, G. W. Kramer, R. G. Christensen and W. A. MacCrehan, *Anal. Chem.* 69 (1997), p. 4783 or Microfluidic devices fabricated in poly(dimethylsiloxane) for biological studies, Samuel K. Sia, George M. Whitesides *Electrophoresis* 2003, 24, 3563-3576.

In some preferred embodiments of the invention, the cartridge is disposable, which is, at least partly, allowed by using suitably priced materials in mass production processes such as continuous embossing (resembling printing). Optionally or alternatively, the cartridge is replenishable, optionally comprising structures or mechanisms to that effect, for example, mechanism for cleaning the microchannel or a structure for replenishing fluid.

FIG. 1A schematically illustrates a perspective partial view of a cartridge 100 with a covered microchannel 102 formed on a substrate 104 having a base surface 156 and top surface 154. Microchannel 102 has a length 112, a horizontal dimension 114 (width) and a vertical dimension 116 (height), as indicated by the respective double-arrows, and is capped by a cover 106 having an interface surface with substrate top surface 154. MicroChannel 102 further illustrates a shadow microchannel, as horizontal dimension 114 is significantly larger than vertical dimension 116. In some embodiments of the invention, horizontal dimension 114 is in the order of magnitude of 100 micrometers and vertical dimension 116 is in the order of magnitude of 10 micrometers.

Figure 1B:
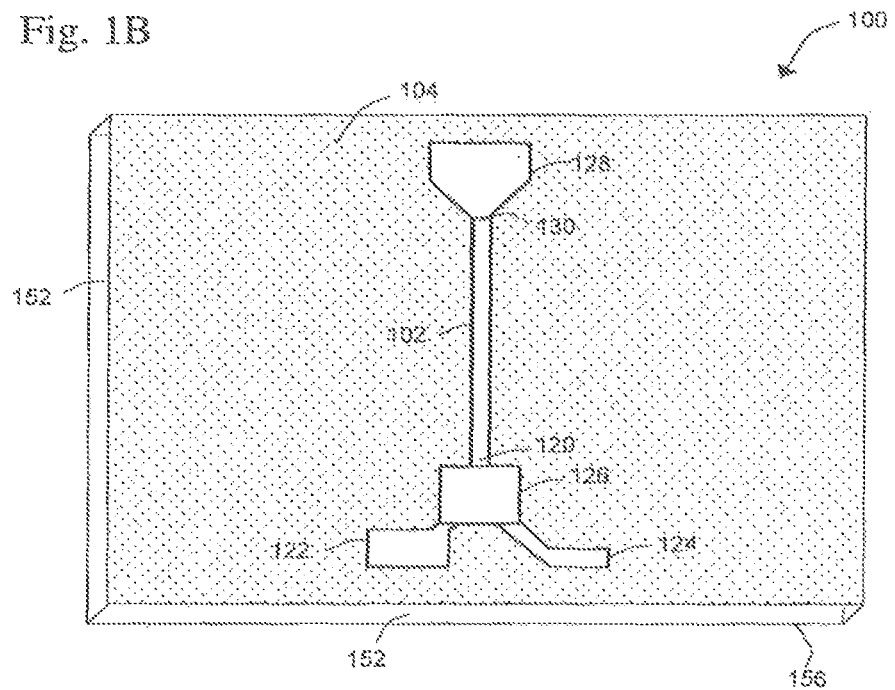
FIG. 1B schematically illustrates a top view of a cartridge with a substrate formed with a microchannel and other microstructures, according to exemplary embodiments of the invention.

FIG. 1B schematically illustrates according to some embodiments a top view of a cartridge 100 having a base surface 156 and side surfaces 152 with a substrate 104 formed with a microchannel 102 and other microstruotures, comprising a fluid inlet 122, a sample inlet 124, a mixing chamber 126 and an outlet chamber 128.

In some embodiments, a viscoelastic fluid is applied or injected to inlet 122, or the fluid is enclosed in inlet 122 during the fabrication of cartridge 100, and the fluid flows from inlet 122 into a connected mixing chamber 126. Optionally, cartridge 100 comprises a plurality of inlets 122, allowing to provide separated constituents of a viscoelastic fluid for subsequent mixing, for example, when beneficial properties of a final viscoelastic fluid may degrade in time or otherwise altered.

In some embodiments, sample inlet 124 comprises a capillary that draws in a fluidic sample comprising a suspension or emulsion of particles, wherefrom the sample flows into mixing a connected chamber 126, optionally or alternatively, a sample fluid is injected or otherwise applied into sample inlet 124.

Fluids that enter mixing chamber 126 are mixed in the chamber and flow into an entrance end 120 of microchannel 102. Optionally, cartridge 100 comprises a plurality of mixing chambers 126 linked to each other and eventually to microchannel 102, such as to provide pre-mixing of some ingredients and subsequent mixing with another ingredient or ingredients. For example, pre-mixing viscoelastic fluid with some additive (e.g. dispersing agents or dyes), and subsequently blend the mixture with the sample.

In some embodiments, outlet chamber 108 is connected with an exit end 130 of microchannel 102 for collecting (draining) the fluid that flowed in microchannel 102.

In some embodiments of the invention, fluids and suspended particles therein am drawn to and flow in microchannel 102 by adhesion and/or by a pressure gradient, without any additional force or field such electric or magnetic or gravitational force (e.g. centrifugal force or field).

In one exemplary variation, the pressure gradient is provided by outlet chamber 128 having a lower pressure than ambient pressure outside the cartridge or relative to the fluid inlet pressure (hereinafter 'vacuum'). Optionally, outlet chamber 128 is or comprises a vacuum chamber. Optionally or alternatively, outlet chamber 128 comprises or connected to a vacuum capsule or pump, such as an elastic miniaturized pump. In some embodiments, the vacuum is isolated from microchannel 102 by a temporary barrier or a valve, so that in order to provide the pressure gradient a connection is produced between outlet chamber 128 and microchannel 102 by breaking the barrier or opening the valve such as by pressing a finger thereon.

In another exemplary variation, the pressure gradient is provided by applying the viscoelastic fluid (or a constituent thereof) in inlet 122 with a pressure larger than the pressure in microchannel 102 and/or outlet chamber 128 (hereinafter 'high pressure'). Optionally, the high pressure is provided by a syringe that applies the fluid to inlet 122. Optionally or alternatively, cartridge 100 comprises a chamber having a high pressure connected to inlet 122 such as by a valve that opens by pressing a finger or other methods. Optionally or alternatively, cartridge 100 comprises a flexible chamber connected to inlet 122 so that by pressing the flexible chamber pressure is applied to inlet 122.

It should be understood by a person skilled in the art that other variations and combinations may be used to provide a pressure gradient to flow the viscoelastic fluid in microchannel 102.

In some embodiments of the invention, the fluid flow rate in microchannel 102 is about the order of magnitude between 0.1 cm/s and 1 cm/s, though the rate may be set, or vary, to other velocities according to conditions such as the fluid composition and properties, the type of the particles and concentration thereof, the apparatus (e.g. a camera capture speed) or operational requirements (e.g. measurement speed).

Cartridge 100 was presented and discussed as a non-limiting example of cartridge having a microchannel. In some embodiments of the invention, microstructures and/or mechanisms additional to the microchannel may vary. For example, in some embodiments, cartridge 100 does not have separate fluid and sample inlets, but rather one inlet where optionally the fluid and sample are mixed, or wherein a mixture of fluid and sample is applied or injected. Or, optionally, cartridge 100 does not have a mixing chamber. Or, optionally, cartridge 100 does not comprise an outlet chamber and the fluid drains out such as via a hole.

Particles and Focusing

Once a viscoelastic fluid with a suspension or emulsion of particles flows into microchannel 102, the particles are aligned in a one- or two-dimensional array parallel to the fluid flow ('Viscoelastic focus').

In case of a shallow microchannel, the particles align in a two-dimensional sheet-like array. In case of a microchannel having identical or similar horizontal and vertical dimensions 114 and 116, respectively, such as having a generally square or circular cross section, the particles align in a generally columnar array.

Pliable particles in a shear flow such as in a viscoelastic flow are deformed responsive to the shear and are aligned in a particular orientation. Red blood cells (RBC), as a particular non-limiting example of particles, are elongated according to the shear stress and ambient viscosity and align in a distinctive orientation in the viscoelastic focus while exhibiting a peculiar dynamic behavior of the external membrane rotating around the interior, as described, for example, in Aviskay Bramky et al., *An automated cell analysis sensing system based on a microfabricated rheoscope for the study of red blood cells physiology, Biosensors and Bioelectronics* 22 (2006) 165-169 and references therein, or in Pozrikidis C. 1995 *Finite deformation of liquid capsules enclosed by elastic membranes in simple shear flow, J. Fluid Mech.* 297, 123-152, Pozrikidis, C., 2003. *Modeling and simulation of capsules and biological cells, or Pozrikidis, C., 2003, Numerical Simulation of the Flow-Induced Deformation of Red Blood Cells Ann. Biomed. Eng.,* 31, 1194-1205.

In some cases or embodiments, fluid flow induced deformations have to be taken into account when the particles shapes are analysed and particularly when quantitative results are derived (see below).

FIG. 1C schematically illustrates a perspective view of a section of microchannel 102 having a width 114 significantly larger than height 116 (shallow microchannel) and having a sufficient length 112 for suspended particles 140 (RBC as an example) to align in a generally planar array, according to exemplary embodiments of the invention.

RBC particles 140 suspended in a viscoelastic fluid (not shown) enter at entrance end 120 of microchannel 102 and flow downstream in a direction indicated by an arrow 144. As particles 140 enter the microchannel they are still disordered but as particles 140 flow downstream they tend to align into a two dimensional array as can be seen about a region in the microchannel indicated by bracket 146. As particles 140 enter a region in the microchannel indicated by bracket 148 and flow downstream, particles 140 form elliptical shapes and are aligned in consistent orientation in a sheet-like array as indicated by horizontal plane 142.

In some embodiments of the invention, particles 140 constitute or comprise other cells. In some embodiments, particles 140 constitute or comprise organic and/or inorganic microspheres or microbeads, optionally with ligands or other compounds such as antigens or antibodies attached to or comprised in the surface or insides the particles, optionally binding to additional compounds such as antibodies or antigens. In some other embodiments, particles 140 constitute or comprise other entities such as minerals, for example, clay particles, optionally with other compounds attached thereon. In some embodiments, particles 140 constitute or comprise fluidic or semi-fluidic particles such as micelles or vesicles.

It should be noted, that once the particles are aligned in an array in a fluid flowing in microchannel, the flow may be halted or stopped such as by reducing or eliminating the pressure gradient, and the particles will remain in an array ('frozen') subject to the buoyancy in the viscoelastic fluid and gravity effects. Since the viscoelastic fluid is viscous, in many cases even if the particles eventually sink to the microchannel bottom, the sinking is sufficiently slow to allow viewing and analysis of the image in an array as described below. Optionally, the particles are fixed (or practically fixed) in place in a motionless fluid by methods such as enlarging the viscosity of the viscoelastic fluid, for example, by cooling (e.g. Peltier effect), or by diffusion of an a suitable chemical agent. Optionally or alternatively, in case the particles have electric dipole or are capable to attain induced dipole, the particles then can be fixed by applying a suitable electric field.

In some embodiments of the invention, the particles are acquired from a biological source, typically from a biological fluid. For example, blood, plasma, lymph, urine, cerebrospinal fluid (CSF) or bone marrow.

In some cases or embodiments of the invention, the particles comprise microbeads (e.g. microspheres) made of or comprising inorganic and/or organic compounds. Optionally, the microbeads comprises or attached to or coated with organic reactive or biologically reactive compounds, that is, compounds that react with or attach to other compounds (e.g. receptors). For example, drugs, antibodies, antigens, enzymes, cells or part thereof (e.g. organelles), hormones or any compound that reacts with or attach to an organic or biological entity. In some cases or embodiments of the invention, the particles comprise cells or part thereof, including optionally blood cells.

In some cases or embodiments of the invention the particles comprise other compounds or physical structures such as clay or other minerals, or micelles, vesicles or any structure having an heterogeneous form in a fluid medium.

The viscoelastic focusing in general and as described below is apt for providing a focused stream of particles for sorters such as Fluorescence Activated Cell Sorting (FACS®). The particles, such as microbeads, comprise of linked or coated with proteins or DNA or RNA or other biological compounds such as antigens or antibodies or other compounds. The particles may be electrically or magnetically charged, for example, by having a magnetic constituent such as a magnetic core, or having ferromagnetic constituents that can be magnetized, or having constituents that can be electrically charged and sustain the charge for a required duration. The beads are focused in an array such as a generally columnar array, and after being singled out, such as by particular fluorescence (e.g. color), the particles are sorted (multiplexed) according to as applied magnetic or electric field. The beads or other particles may also be used in ELISA (Enzyme-Linked-ImmunoSorbant-Assay) such as when the particles are coated or bind with enzymes for the linking with (or cleaving) the target compound or compounds, and may subsequently be sorted as, for example, described above.

Optical Viewing

As particles 140 are aligned about plane 142 in consistent shapes and orientation, particles 140 can all (or at least the greater part thereof) be optically focused and viewed by a magnifying optical system (objective). Since particles 140 vertical dispersion (i.e. parallel to dimension 116 of FIG. 1C) is practically negligible, objective can be simplified by design tradeoff as depth of field requirements are relaxed or even dispensed with.

In some embodiments, particles 140 are illuminated from a direction across the objective, that is, through the microchannel (bottom lighting). Optionally or alternatively, particles are illuminated above the microchannel (top lighting).

In some cases or embodiments of the invention, the particles are clearly visible and distinguishable against the underlying medium (e.g. fluid, substrate). In some other cases or embodiments, the particles are not distinguishable and are enhanced such as by polarized lighting or other methods of the art such as dark field.

In some embodiments, some coloration techniques are used to enhance and/or distinguish particles 140. For example, when leukocytes suspension is used, the leukocytes may be stained and differentiated by acquiring different colors. In case a suspension of non-living leukocytes is adequate then stains such as common in the art may be used, for example, Wright (CAS NO. 68988-924) or Giesma (CAS No. 67-56-1). Optionally or alternatively, when a suspension of living leukocytes is required then stains such as Astrazon orange G (CAS No. 3056-93-7), or Neutral red (CAS No. 553-24-2) or Griefswalders blue may be used (which are dissolvable in water and do not require washing), see, for example, U.S. Pat. Nos. 458,122 and 4,400,370.

In some embodiments, the light is of a particular range (color) in an Infrared and/or visible and/or ultraviolet region, optionally comprising a combination of colors. In some embodiments, the light is monochromatic, e.g., having a narrow bandwidth relative to the respective region such as smaller than 100 nm or 50 nm. Using monochromatic light allows to further simplify the objective by design tradeoff as color aberrations correction requirements are relaxed or even dispensed with.

Using visible light, particles 140 may be optically viewed manually, such as by an objective and an eyepiece, or with a camera such as a digital still or video camera that links to the objective and reproduces images on a display and/or printouts. Using IR or UV radiation, however, an auxiliary equipment is required such as a camera with a sensor responsive to UV or IR radiation.

It should be noted that referring to a two-dimensional array (sheet) such as 142 of FIG. 1C is applicable as well to a one-dimensional array (column), while allowing for the geometrical differences.

Reader

A cartridge with viscoelastically aligned particles in a one- or two-dimensional array in a microchannel (hereinafter an 'active' cartridge) is generally and without limiting represented in the discussion below and corresponding drawings by cartridge 100 with particles 140 flowing through microchannel 102 as described above with respect to FIGS. 1A-C.

In typical embodiments of the invention, cartridge 100 is placed in a reader where the particles shapes are reproduced by an objective and electronically captured for viewing on a monitor and/or for handling by an image processing and/or analysis apparatus.

Figure 2A:
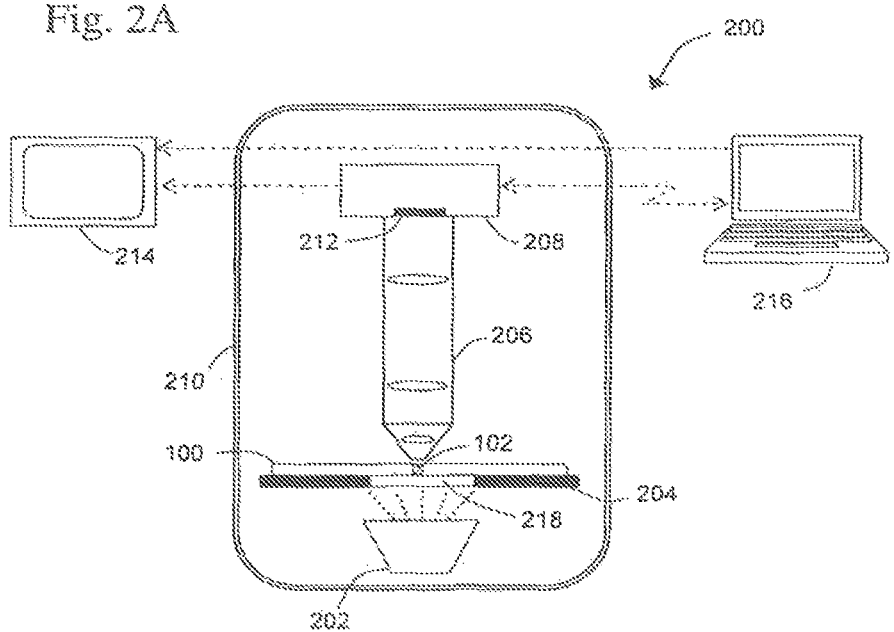
FIG. 2A schematically illustrates a reader and components thereof, according to exemplary embodiments of the invention.

FIG. 2A schematically illustrates a reader 200 and components thereof, comprising an illumination source 202, a cartridge holder 204 ('holder'), an optical objective 206 (figuratively indicated by lenticular elements therein), and an image acquisition device 208 ('camera'). Reader 200 is further equipped with a power supply, connection wires and contacts as required (not shown).

Active cartridge 100 is removably attached to holder 204 which fixedly holds the cartridge to enable a steady focusing of objective 206 at the particles array (e.g. array 142 in FIG. 1C). Illumination source 202 provides light that passes through holder 204 and through the cartridge and at least partly through the particles, and objective 206 optically projects the particles image on an image sensor 212 (e.g. CMOS or CCD) in camera 208. Camera 208 captures the image off image sensor 212 and provides the image, possibly after a transformation and/or pre-processing, to a monitor (screen) 214 for a visual observation. Additionally or alternatively, camera 208 transfers the image to a computer 216 which processes the image and optionally analyzes it to provide one or more qualitative or quantitative results. Optionally or alternatively, monitor 214 receives the image from computer 216 (rather than from camera 208), optionally after processing such as enhancement, background reduction or other visual effects known in the art. Optionally or alternatively, monitor 214 comprises a part of computer 216.

In some embodiments, the results are presented on monitor 214, optionally or alternatively, reader 200 comprises a printer (not shown) and computer 216 optionally provides a printout of the results or part thereof and/or an image of the particles or part thereof.

In some embodiments, camera 208 captures the particles image in a video mode, namely, as a sequence of images while the particles move with the viscoelastic fluid in the microchannel. Optionally or alternatively, a sufficiently rapid image acquisition is used while the particles move with the viscoelastic fluid in the microchannel. In some embodiments, the flow of the viscoelastic fluid is halted and the particles are fixed as described above, so that only one (or few) captures are acquired.

Illumination source 202 provides light in a suitable color to produce an image of good quality, for example, an image having best attainable or sufficient or reasonable sharp and/or distinct and/or contrasted shapes of the particles. In some embodiments, the light is monochromatic and optionally the color is selected from a pre-set group or according to the capabilities of illumination source 202. Optionally or alternatively, the color is variably set, such as according to the nature and/or color of the particles. In some embodiments, the light is polarized or provided as dark field or other illumination techniques used in the microscopy art.

In some embodiments, illumination source 202 illuminates cartridge 100 on holder 204 from above and objective 206 projects on sensor 212 an image according to light reflected from the particles in the microchannel. Optionally or alternatively, reader 200 comprises two or more light sources 202 which illuminate from below and/or above of the cartridge in colors and intensities to increase or maximize the quality of the particles image (such as in terms of sharpness, contrast, etc.), Optionally, reader 200 comprises a light source 202 that illuminates the cartridge obliquely or from the side (perpendicular or in acute angle to cartridge 100 thickness surface (such as surfaces 152 FIG. 1B).

In some embodiments of the invention, light source 202 comprises at least one solid-state light source unit. In some embodiments, a solid-state light source unit comprises one of a LED, OLED, PLED or one of other electro-luminescence devices (hereinafter 'LED').

In some embodiments, holder 204 is fabricated or formed such as to aid in illumination of the particles in active cartridge 100 held by holder 204. For example, holder 204 comprises at least one of a light diffuser or a filter or a polarizer or a collimator (e.g. Fresnel lens) below the microchannel in the active cartridge such as in a region 218 of holder 204. In some embodiments, holder 204 comprises a LED or a plurality of LEDs in a similar manner as cartridge 100 comprises a LED or a plurality of LEDs as described below and illustrated in respective FIGS. 3A-C (and not repeated for brevity and clarity).

In some embodiments, cartridge 100 comprises one or more LEDs that illuminate microchannel 102.

Figure 3A:
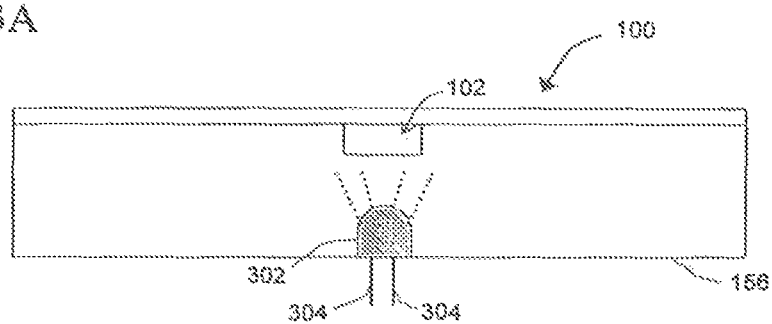
FIG. 3A schematically illustrated a cartridge having a microchannel and comprising a LED opposite the microchannel, according to exemplary embodiments of the invention.

FIG. 3A schematically illustrated a cartridge 100 having a microchannel 102 and comprising (or connected with) a LED 302 at the lower part of the cartridge opposite the microchannel, LED 302 is driven through electric contacts 304 and illuminates microchannel 102. Optionally, LED 302 comprises a diffuser and/or translucent cover to provide uniform or approximately uniform illumination. Optionally, LED 302 represents a plurality of LEDs disposed about the lower surface 156 of cartridge 100.

Figure 3B:
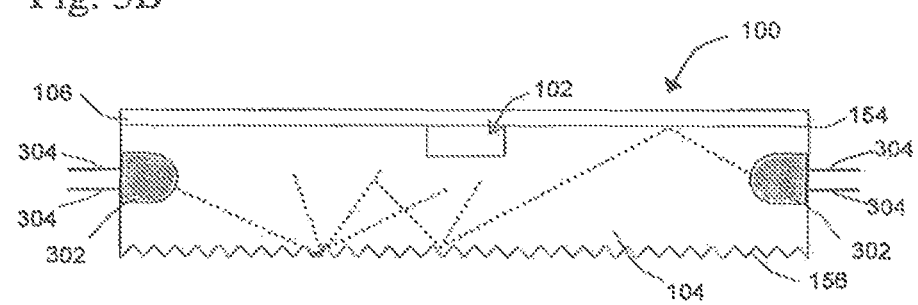
FIG. 3B schematically illustrated a cartridge having a microchannel and comprising LEDs disposed at the sides of the cartridge, according to exemplary embodiments of the invention.

FIG. 3B schematically illustrated a cartridge 100 having a microchannel 102 and comprising (or connected with) LEDs 302 disposed at the sides of the cartridge. An interface layer 154 about the upper surface (or part thereof) of substrate 104, or the lower surface of cover 106 (or part thereof) is reflective, such as by a suitable coating or selection of refraction indexes of the materials. Light emitted by LEDs 302 that hit layer 154 is reflected towards the lower surface 156 of cartridge 100 (or of substrate 104). Surface 156 is reflective such as by coating and reflects light reflected by layer 154 or light directly emitted by LEDs 302 and directs the light upwards towards microchannel 102. Optionally, layer 156 is corrugated or ground or translucent so that layer 156 reflects diffused or scattered light that assist in informing the illumination of microchannel 102. Optionally layer 154 is also diffusive or translucent and scatters the reflected light therefrom, further assisting in informing the illumination of microchannel 102.

Figure 3C:
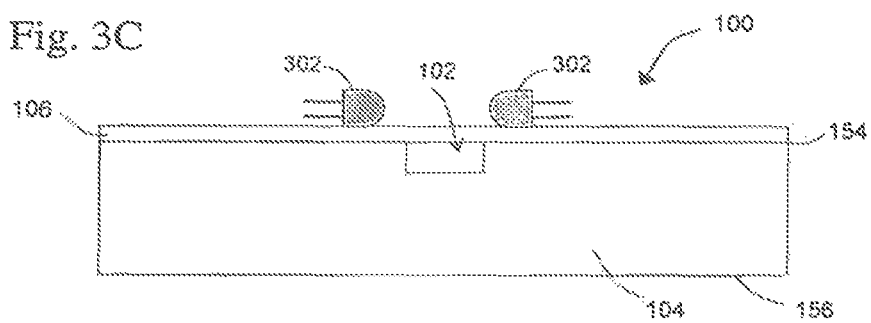
FIG. 3C schematically illustrated a cartridge having a microchannel and comprising LEDs at the oa the cover of cartridge at each side of the microchannel, according to exemplary embodiments of the invention.

FIG. 3C schematically illustrated a cartridge 100 having a microchannel 102 and comprising (or connected with) LEDs 302 at the on cover 106 at each side of the microchannel. FIG. 3C illustrates another variation of illuminating microchannel 102. It should be understood that the number of LEDs and location and direction thereof as well as the nature of reflecting and diffusing or scattering surfaces may be varied to achieve an illumination suitable for general and/or particular requirements.

In some embodiments, as an addition or alternative to LEDs 302 illumination and diffusing and scattering of light as described above with respect to FIGS. 3A-C may be carried out by other light sources such as point bulbs, fiberoptic guides or other apparatus, all of which generally, without limiting, are represented by light source 202 in FIG. 2A.

In some embodiments of the invention, cartridge 100 is held by holder 204 in a pre-set position such that objective 206 is focused at the aligned particles without any further adjustments. Optionally or alternatively, objective 206 is automatically focused at the aligned particles, wherein the focusing is controlled and/or driven by camera 208 and/or computer 216, such as by maximizing the contrast or other features of the image. In some embodiments, the auto focusing is carried out by moving a mechanism attached to objective 216 or components therein (e.g. varying distance between optical elements in the objective). Optionally or alternatively, holder 204 is moved relative to objective 206. Optionally or alternatively, manual focusing is performed by observing an image displayed on monitor 214 or using an optional auxiliary eyepiece. In some preferred embodiments, the focus is not altered, or negligibly altered, when cartridges are placed and released as part of using reader 200, and only occasionally, or following an operation or service protocol, focusing is checked and/or adjusted.

In some embodiments of the invention, reader 200 provides one or more of the functionalities of cartridge 100 microstructures. For example, providing pressure gradient by vacuum apparatus that connects to outlet chamber 128 as cartridge 100 is disposed and fitted on holder 204. Or as another example, providing viscoelastic and/or additives reservoir that connects to fluid inlet 122 as cartridge 100 is disposed and fitted on holder 204.

In some preferred embodiments of the invention, cartridge 100 is a disposable article and is routinely removably placed in reader 200, resembling using a microscope slide.

In some embodiments, cartridge 100 is replaceable in the sense that cartridge 100 can be swapped with other equivalent or compatible cartridges as a routine work procedure. Optionally, cartridge 100 is routinely removably placed in reader 200 as a replenishable cartridge, having structures that facilitate operations such as cleansing, refilling a fluid or replenishing vacuum, wherein at least part of which are provided in reader 200. In alternative embodiments cartridge 100 is typically comprised as a part of reader 200 and replaced according to service protocol or malfunction, wherein reader 200 provides functionalities such as viscoelastic fluid supply, pressure gradient and cleaning.

Holder 204 facilitates removably holding or removably attaching or removably gripping (collectively denoted as 'gripping') cartridge 100 in reader 200 by methods or mechanisms such as sliding under resilient strip or strips, a clip (resembling paper clip), a gripper (like pliers), a snap fastener, matching holes with pins, or fitting into a receptacle, or any suitable releasable fastener or mechanism.

In some embodiments of the invention, cartridge 100 is mechanically and/or optically compatible with a microscope slide, optionally as a slide with a cover. For example, cartridge 100 can be attached to an optical microscope and viewed as a conventional slide is viewed, either through an eyepiece or aided by a camera and optionally other devices such as a computer.

Preferably, in some embodiments, light source 202 is coordinated with camera 208 such that light source 202 illuminates only for the duration of capturing an image. Coordination (synchronization) of light source 202 and camera 208 may be advantageous such as by avoiding possible over heating and possible deforming of cartridge 100 or particles 140 and/or avoiding possible photo-degradation of particles 140 and/or saving power which may be significant in battery powered reader 200. Optionally, light source 202 is dimmed when camera 208 is not capturing to allow viewing of cartridge 100.

Referring back to FIG. 2A, in some embodiments of the invention, illumination source 202, holder 204, objective 206 and camera 208 are packaged in a case 210 having an access to grip active cartridge 100 to holder 204. Optionally, computer 216 and/or monitor 214 and/or the printer (not shown) are also packaged in case 210. Optionally or alternatively, computed 216 and monitor 214, and optionally the printer (not shown), axe packaged together outside case 210.

Compact Reader

In some preferred embodiments of the invention, reader 200 is constructed as a compact apparatus comprising the operational elements as densely packed components to reduce the size of reader 200. The compact construction may allow using reader 200 as a desktop unit, or ambulatory unit or as a portable unit, optionally a battery operated unit, while possibly compromising some cost and/or performance.

Figure 2B:
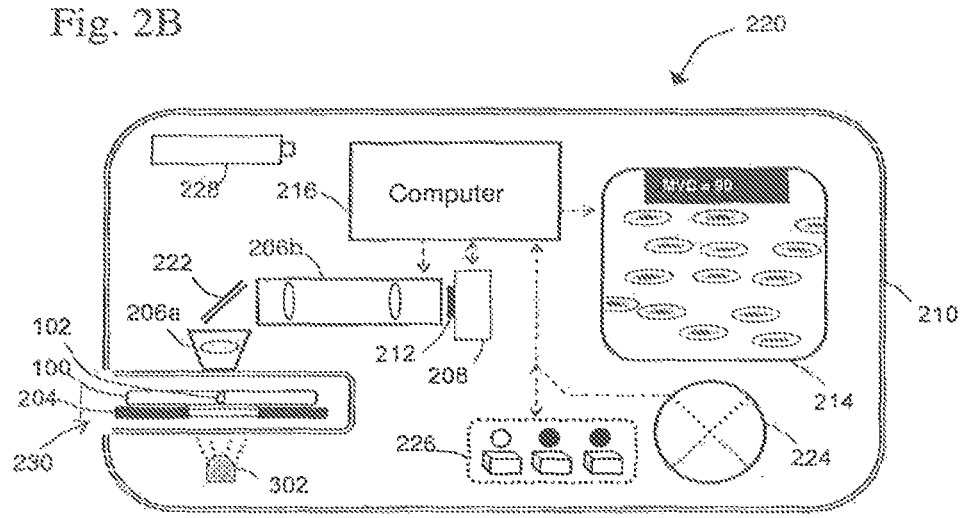
FIG. 2B schematically illustrates a compact reader and components thereof, according to exemplary embodiments of the invention.

FIG. 2B schematically illustrates a compact reader 220 and components thereof, according to exemplary embodiments of the invention. Akin to reader 200 of FIG. 2A and with components resembling or equivalent to the components thereof, reader 220 retains, without limiting, some features and/or capabilities and/or functionalities of reader 200 as described above. For clarity and brevity, only particular characteristics of some embodiments of compact reader 220 are generally discussed below.

In some embodiments of the invention, reader 220 comprises:

(a) A case 210 with an opening 230 for cartridge insertion. Preferably, case 210 is configured and designed for convenient handling and operating (see below), optionally with operation-related or appealing coloring and shape.

(b) A cartridge holder 204 configured for a convenient removable gripping of an active cartridge 100, such as by a mechanism for snap locking and bouncing release, or any other mechanism for simple and comfortable insertion and fixing and subsequent simple and easy release of active cartridge 100.

(c) A light source, preferably as one or more LEDs 302 illuminating through microchannel 102 in cartridge 100 with a selected or determined color. Optionally, such as according to some particular application or particle type, one or more LEDs 302 illuminates microchannel 102 from other or additional directions. Generally, without limiting, LED 302 represents also other light source, preferably miniaturized such a fiberoptic guide (see also light source 204 above respective to reader 200 of FIG. 2A).

(d) An objective 206, possibly divided into two parts 206a and 206b with a folded optical path by mirror 222 enabling the compact configuration of reader 220. Objective parts 206a and 206b and mirror 222 represent optional more parts and elements designed for a compact configuration of reader 220.

(e) An image acquisition device 208 comprising a light sensor 212 that captures the image of illuminated microchannel 102 and of particles therein. Preferably image acquisition device 208 is a miniaturized camera or custom device designed for particular requirements and small size and/or power consumption.

(f) A display screen 214 on an external surface of case 210, such as an LCD screen, preferably as a color display.

(g) A four-way button 224 and a group 226 of switches (rectangles)/lights (circles) on an external surface of case 210, representing any element or elements for controlling, operating or interacting with reader 220 components or operation, as known in the art of instruments operation or otherwise developed.

(h) One or more processors with required memory and other peripheral components and mechanism ('computer') 216 executing one or more furnished programs related to operating and controlling reader 220 and one or more programs related to image processing and other optional applications. In typical preferred embodiments, computer 216 interacts with and/or controls, inter alia, image acquisition device 208, screen 214, illumination source 302, control elements 224 and 226 and an optional motion mechanism of objective 206 for auto focusing on particles in active cartridge 100.

(i) Power supply, represented by figurative battery 228, that distributes electric power to components of reader 220, such as computer 216, display 214, LED 302, interaction elements 224 and 226. Optionally, power is provided also to objective 206 and/or mirror 222 in order to move for proper focusing and/or changing magnification. In some embodiments, power supply 228 is connected to a mains source. Optionally or alternatively, power 228 is battery or batteries driven, optionally by rechargable battery or batteries. (Power distribution is not shown).

Optionally, reader 220 further comprises a miniaturized printer, such, as one using a thermally sensitive paper.

As a typical non-limiting illustration, computer 216 senses settings such as modes selection from buttons of group 226 or presents a menu on display 214 where selections such as mode settings are made by four-way button 224. Computer 216 receives the image from image acquisition device 208 and, according to reader 220 settings, processes the image while concurrently or subsequently displaying the image or part thereof, or processed part thereof, on screen 214. According to reader 220 settings, computer 216 performs one or more particular analysis on the processed or original image (or as part of the image processing) and presents the results on screen 214, either graphically and/or alphanumerically. Modes or setting of reader 220 may be indicated on screen 214 and/or lights of group 226. For operational convenience, as an optional mode of reader 220, once cartridge 100 is gripped properly on holder 204, a sensor (e.g. electric contact or optical or magnetic sensor) indicates to computer 216 to capture the image in microchannel 102 and proceed with image processing and/or analysis.

In some embodiments, optionally to reduce space (and optionally cost, at least in mass production), camera 208 and computer 216 are combined into a single unit (or compound unit), optionally comprising one or more integrated circuits (e.g. CMOS comprising image sensor, processor and auxiliary devices such as memory and input/output ports).

In some embodiments, reader 220 is in a default mode when powered on, for example, in a mode when inserting a cartridge it acquires the image and performs a pre-set processing and analysis and displays a pre-set image and data on the screen.

In some embodiments, reader 220 comprises an interface apparatus and/or mechanism (e.g. comprising software) to link with other computers or devices (not shown) for operations such as data storage, retrieval, or statistical analysis or other operations as required.

It should be noted that features or capabilities or functionalities described with respect to reader 220 are, in some embodiments, applicable to reader 200, which represents, without limiting, a generalized reader for active cartridge 100.

Kit

In some embodiments of the invention, one or more cartridges are provided as a kit. Generally and without limiting, a cartridge is represented in the discussion below and corresponding drawings by cartridge 100 as described above with respect to FIGS. 1A-C.

Figure 4A:
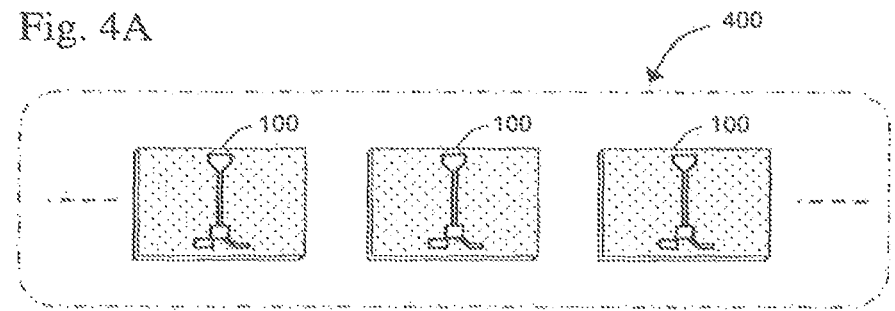
FIG. 4A schematically illustrates a kit comprising a plurality of cartridges, according to exemplary embodiments of the invention.

FIG. 4A schematically illustrates a kit 400 comprising a plurality of cartridges 100. In some embodiments, cartridges 100 are empty (without any fluids or particles or other constituents such as vacuum capsule). Optionally, cartridges 100 comprise vacuum such as a vacuum capsule or chamber or outlet chamber 128 is vacuumed to provide a pressure gradient (as described above). Optionally or alternatively, cartridges 100 comprise a viscoelastic (or constituent thereof) such as in inlet 122.

Figure 4B:
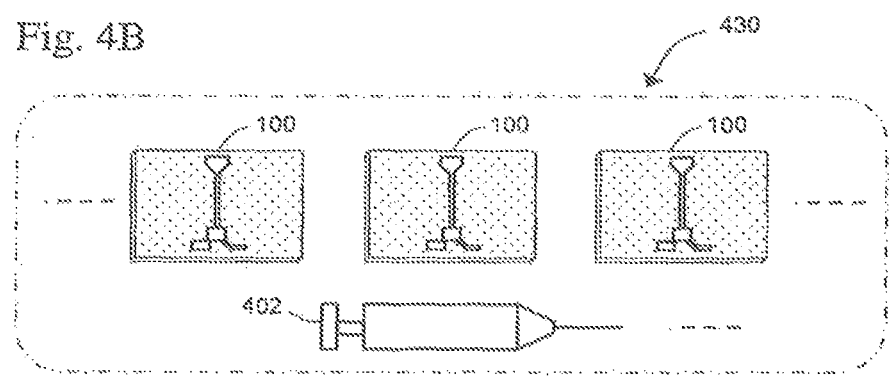
FIG. 4B schematically illustrates a kit comprising a plurality of cartridges and one or more fluids in one or more syringes, according to exemplary embodiments of the invention.

FIG. 4B schematically illustrates a kit 430 comprising a plurality of cartridges 100, optionally similar or identical to kit 400, and further comprising a one or more fluids, such as a ready for use viscoelastic fluid or a constituent thereof. In some embodiments, a fluid is provided in a syringe 402 which may be used to inject the fluid into inlet 122 of cartridge 100. Optionally or alternatively, a plurality of syringes is provided, containing the viscoelastic fluid and/or or constituents for making a required viscoelastic fluid.

Figure 4C:
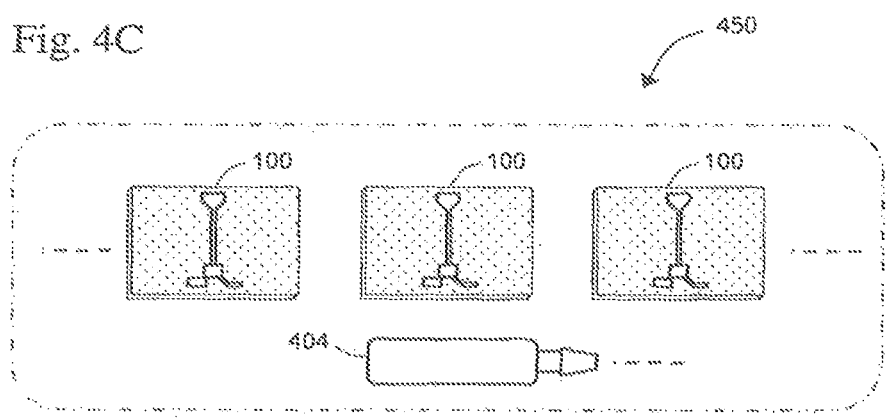
FIG. 4C schematically illustrates a kit comprising a plurality of cartridges and one or more fluid constituents in one or more containers, according to exemplary embodiments of the invention.

FIG. 4C schematically illustrates a kit 450 comprising a plurality of cartridges 100, optionally similar or identical to kit 400 or 430, and further comprising one or more fluids in one or more containers 404, such as bottles or tubes (e.g. like toothpaste tube). The one or more fluids comprise a ready for use viscoelastic fluid or a constituent thereof.

In some embodiments, some or all the fluids in a kit are provided as powder, or as other forms such as gels, which are subsequently dissolved in another fluid, such as a viscoelastic fluid constituent or a solvent such as water or alcohol or any solvent, where the solvent is optionally provided as a part of the kit or as an additional element. In some cases the constituents are provided separately in the kit since a ready for use fluid may degrade in time and/or due to environmental conditions such as temperature, or when variants of the viscoelastic fluid may be prepared for various purposes, for example, adding compounds to prevent aggregation or coagulation of certain particles (e.g. RBC) or adding staining agents for differentiating leukocytes.

In some embodiments of the invention, a kit comprises any combination or variants of the kits 400, 430 or 450 illustrated in FIGS. 4A-C, wherein a dashed line represents any number of the adjunct articles (e.g. cartridge 100) in a kit (including a single article).

In some embodiments, a kit comprises a reader such as compact reader 220 of FIG. 2B.

In some embodiments, a kit comprises a user guide comprising operational instructions as text and/or illustrations and optionaiiy comprising safety measures.

In some embodiments, the kit comprises a case, preferably configured for quick and convenient access and handling of the components thereof.

Methods

Methods for observing and/or analyzing particles according to some embodiments of the invention are described below with respect to FIGS. 5 and 6.

FIG. 5 schematically illustrates a flowchart outlining actions in observing a magnified image of particles aligned in viscoelastic fluid according to some embodiments of the invention.

Microscopic particles, such as blood cells or beads, are suspended in a viscoelastic fluid having properties for aligning the particles in a microchannel (502).

The fluid is flowed in a microchannel having dimensions appropriate for aligning the particles in a one or two-dimensional array thereby aligning the particles accordingly (504).

A lens, such as a microscope objective, optionally with an eyepiece, is focused at the particles array in the microchannel (506) and a magnified image of the particles shapes is observed (508).

Optionally, the particles are analyzed, such as for shapes, concentration, density or any other derivation (510).

FIG. 6 schematically illustrates a flowchart of actions for capturing and analyzing a magnified image of particles aligned in viscoelastic fluid according to some embodiments of the invention.

A substrate formed with at least one microchannel (602) and a viscoelastic fluid adapted for aligning particles in at least one-dimensional array in the microchannel (604) and particles for observation and/or analysis (606) are provided.

The particles are suspended in the viscoelastic fluid (608) and the suspension is flowed in the microchannel thereby aligning the particles in one- or two-dimensional array (610). In some embodiments, the flowing the fluid is effected, at least partially, by applying a pressure gradient, preferably without any externally applied electric or magnetic or centrifugal or gravitational force.

An optical apparatus such a magnifying objective focused at the array is used to form (i.e. generate) an image of the particles in the microchannel (612) and the image is captured by an image acquisition device such as a camera (614).

The captured image of the particles is transferred to a computing device that executes a furnished program configured to analyze particles in the captured image (616), and the results of the analysis are provided by the computing device (618), such as by a display monitor and/or printout.

Program Functionality

In some embodiments of the invention, the computing device, such as a computer (or processor) linked with or built-in a reader such as reader 200 or 220 of FIG. 2A or 2B, respectively, is provided with one or more programs for execution by the computer, including, inter alia, one or more programs of the following functionalities:

Pre-Processing

Modification of the image or regions thereof for better quality or intelligibility. For example, filtering background noise or reducing the background, or sharpening the image or contents thereof (e.g. particles shapes) or other operations such as modifying contrast or brightness or other parameters for enhancing the image quality or clarity, such as color.

Image Processing (Analysis)

Extracting Information embedded in the image. For example, segmentation or blob analysis, isolating and/or extracting and determining the shapes or morphology of the particle, at least generally or approximately, such as round, elongated, branching, fiber-like, fibrous, helical, or looping, or determining features such as convexity or eccentricity. Optionally the program subsequently determines the types of the particles (e.g. identification) of the particles, for example, leukocytes types according to staining colors, as described above.

In some embodiments, based on shapes of regions of the image and/or on extracted particles shapes the program provides calculations or estimations of the sizes and/or volumes and/or density and/or concentration of the particles.

In some embodiments and cases, the program provides quantitative results (e.g. concentration of particles). Optionally or alternatively, the program provides qualitative results (e.g. particle type). Optionally, the program provides both quantitative and qualitative results.

In some embodiments, the program provides values based on one or more derivations and/or manipulations of extracted or determined features (e.g. size of particles). Optionally the derivation comprises employing experimental or assumed values such as known in the art and/or derived from a calibration procedure or otherwise obtained.

Optionally, based for example on the shape or size or concentration of the particles or other determined data, the program provides a value or as indication or a suggestion of at least one of a biological or clinical significance, for example, inference or indication of possible or plausible physical or physiological or pathological condition.

In some embodiments, when the particles comprise biological entities or samples, the program provides at least some measurements or evaluations as are common in the clinical or biological art.

For example, in some embodiments, the particles comprise red blood cells (RBC) and the program provides results such as RBC Count (e.g. CSC), Packed Cell Volume (PCV), or Mean Corpuscular Volume (MCV) or derivatives or related quantity thereof, such as Red Cell Distribution Width (RDW) or Hemoglobin related results such as Mean Corpuscular Hemoglobin Concentration (MCHC). In some embodiments, the particles comprise white blood cells (WBC) and the program provides results such as differential white blood cells counts, or blood platelets count (PLT) or derivatives or related quantity thereof.

As another example, in sense embodiments, cerebrospinal fluid (CSF) sample is used to analyze for leukocytes, and particularly neutrophils, or polymorphonuclear leukocytes and infectious agents, cell debris, and tissue fluid formed at the site of infection or injury (pus cells) for assessing the possibility of meningitis. The leukocytes or other cells or entities are, optionally, stained to differentiate and identify and/or quantify in order to have a reasonable assessment of meningitis.

As yet another example, lymphocytes from lymph or bone marrow may be distinguished by the presence of a number of receptors and differentiation antigens, or lymphoma and/or leukemia cells are distinguished, and analysis and optional quantification is carried to provide an assessment of leukemia.

Accordingly, in some embodiments, other samples and particles may be used. For example, urine tested for bacteria (bacterial infection), or amniotic fluid tested for particles having lamellar body diameter in the range of micrometers (which typically are not detectable in US) and lamellar body counts (LBCs) may be provided such as for assessing fetal lung maturity.

Auto-Focus

Auto-focus of an optical lens or objective based on maximal contrast or sharpness (at least at a particular region of interest). The objective or components thereof or the sample (e.g. cartridge) are moved to maximize the focusing such as by a mechanism controlled by the computer responsive to the focusing as determined by the program. For example, the program may implement a function that quantifies sharpness, such as a Laplacian of a Gaussian (LoG) and vary the focus to maximize the LoG function.

In some embodiments of the invention, when the particles comprise cells or other biological entities such as microbeads with attached antigens or other compounds such as drugs, the measurement comprise values or indications of a chemical or biological or medical or clinical significance, such as known in the art of biological or medical tests and/or analysis and/or assessment.

Display

Image display, such as settings pixels of a screen or monitor (e.g. screen 114 of FIG. 2A or 2B, or printing on a paper.

Operation & Control

Operation and control of a reader such as reader 200 or 220 of FIG. 2A or 2B and components thereof, such as controlling image capture by a camera, sensing manual control (e.g. buttons or menu selection), or interaction with an optional external computer.

Algorithms

In some embodiments, the image related program or programs are based on or implement algorithms or methods of the art, such as in B. Jahne, *Practical Handbook on Image Processing for Scientific Applications*, CRC Press, 1977, or J. C. Russ, *The Image Processing Handbook*, CRC Press 1995, or A. K. Jain, *Fundamentals of Digital Image Processing*, Prentice Hall int. 1989, or numerous books, articles and publications of image processing, pattern recognition, and applications thereof. In many cases neural networks are used for cells image analysis and pattern recognition optionally involving also fuzzy logic. For example, C. H. Chen, *Fuzzy logic and neural network handbook* Mcgraw-Hill Computer Engineering Series, 1996 (ISBN:0-07-011189-8), and many other related publications.

Exemplary Experiments

Experiment I

A microchannel, made of PMMA (polymethylmethacrylate) having a width (horizontal dimension) of 200 µm and height (vertical dimension) of 20 µm was prepared by hot embossment.

A viscoelastic solution of 0.6% w/v PAA (AP30) was dissolved in 1 ml PBS (pH 7.4) and 1.5 mg/ml EDTA and was promptly mixed with 20 µL of whole blood from a fingertip, yielding a suspension of blood particles.

The suspension was infused into and flowed in the microchannel under a negative gradient (vacuum) where the cells were aligned ('focused') in a layer at the center of the microchannel under various pressure gradients.

Figure 7:
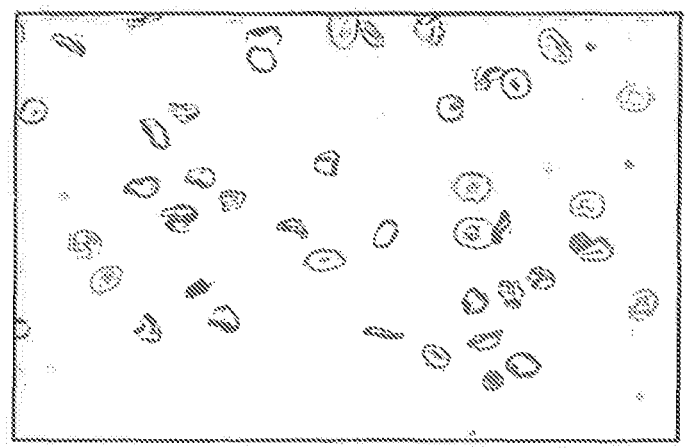
FIG. 7 shows an image (after pre-processing) of blood cells aligned in a viscoelastic fluid flow in a microchannel as in Experiment I, according to exemplary embodiments of the invention.

FIG. 7 shows an acquired image of blood cells aligned in a viscoelastic fluid flow in a microchannel under experiment conditions as described above (Experiment I).

For clarity, the image was pre-processed by operations such as level equalization, brightness/contrast adjustments and background reduction.

Red blood cells are clearly in focus (optical focus at a viscoelastic focused particles) with some minor aggregation. Several echinocytes (morphologically altered red blood cells) are visible due to the pH level being higher than about 7.4.

Based on acquired images such as of FIG. 7, the cells concentration can be obtained by a formula:

$$Con = N \times D / (FOV \times H)$$

Where:
Con is the concentration of RBC;
N is the number of RBC;
D is dilution of the RBC;
FOV is the optical field of view area; and
H is the height of the microchannel.

An individual RBC volume may be obtained from acquired images by calculating the area of an RBC and multiplying by an empirical factor and MCV may be obtained by averaging the volumes of the RBC.

Experiment II

Using a microchannel as in Experiment I above, blood from a fingertip was mixed in a solution of 0.8% w/v Dextran 40 kDa, 100 ppm of PAA AP45, 9.52 g/L HEPES, 0.90 g/L Glucose (Dextrose) and 7.00 g/L NaCl, yielding a suspension of blood cells which was flowed in the microchannel.

Figure 8:
FIG. 8 shows an image (after pre-processing) of blood cells aligned in a viscoelastic fluid flow in a microchannel as in Experiment II, according to exemplary embodiments of the invention.

FIG. 8 shows an acquired image of blood cells aligned in a viscoelastic fluid flow in a microchannel under experimental conditions as described above (Experiment II).

For clarity, the image was pre-processed by operations such as level equalization, brightness/contrast adjustments and background reduction.

The blood cells are clearly in focus, though considerable aggregation occurs (tor example, relative to Experiment I), yet individual cells can still be differentiated. Using 500 kDa Dextran, rather than 40 kD as above, eliminated the aggregation.

Experiment III

A solution of 5 µl aqueous of 1% Basic Orange 21 and 0.1% Neutral Red dyes were dissolved in DI water and mixed with 25 µl of whole blood. The solution was subsequently dissolved in a 1:50 ratio in a solution of 0.6% w/v PAA (AP30) and further dissolved in PBS (pH 7.4) and 1.5 mg/ml EDTA 1, yielding a suspension of blood cells. The suspension was flowed in the microchannel of 50 µm width and 200 µm height as described above for Experiment I.

The blood cells were aligned in the microchannel and the cells were differentially stained by the dyes (see above). Using known image processing techniques, such as described above, it was possible to count and distinguish the individual 5 types of Leukocytes: Neutrophils, eosinophils, basophile, lymphocytes and monocytes.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A blood analyzer, comprising:
a) a case;
b) holder, associated with the case, the holder being configured to retain a blood analysis cartridge, the blood analysis cartridge comprising at least one mixing chamber and being configured to accept a blood sample, wherein the blood analysis cartridge is further configured to enable flow of a mixture including a viscoelastic fluid and at least a portion of the blood sample through a microchannel, wherein a width of the microchannel is larger than a height of the microchannel, such that blood cells from the at least a portion of the blood sample align in a focusing region in a two-dimensional array of the blood cells;
c) an image acquisition device, associated with the case, the image acquisition device defining an optical path configured to intersect the focusing region when the blood analysis cartridge is retained in the holder; and
d) at least one processor configured to receive from the image acquisition device images of the two-dimensional array and determine, based on the images of the two dimensional array, at least one of blood cell count, blood cell concentration, blood cell size, blood cell shape, or blood cell type.

2. The blood analyzer of claim 1, wherein the blood analysis cartridge is disposable.

3. The blood analyzer of claim 1, wherein the at least one processor is further configured to differentiate between and enable blood cell counts of neutrophils, lymphocytes, monocytes, eosinophils, and basophils.

4. The blood analyzer of claim 1, wherein the at least one processor is further configured to enable separate blood cell counts of neutrophils, lymphocytes, monocytes, eosinophils, and basophils.

5. The blood analyzer of claim 1, wherein the holder is configured to releasably grip the blood analysis cartridge.

6. The blood analyzer of claim 1, further comprising an illumination source configured to illuminate the two-dimensional array.

7. The blood analyzer of claim 6, wherein the light source comprises at least one light source unit and produces light in a combination of colors.

8. The blood analyzer of claim 6, wherein the light source comprises a solid state light source.

9. The blood analyzer of claim 1, wherein each of the at least one mixing chambers includes viscoelastic fluid comprising at least one high molecular weight polymer.

10. The blood analyzer of claim 1, wherein each of the at least one mixing chambers is at least partially flexible and pressable.

11. The blood analyzer of claim 1, wherein the image acquisition device is configured to capture the images of the two-dimensional array as a sequence of images while the mixture moves through the focusing region.

12. The blood analyzer of claim 1, further comprising a vacuum apparatus for providing a pressure gradient to flow the mixture through the microchannel in the cartridge.

13. The blood analyzer of claim 1, wherein the at least one processor is configured to determine a concentration of blood cells according to the formula $$Con = \frac{N \times D}{FOV \times H}$$

where Con is concentration of cells; N is number of cells; D is dilution of cells; FOV is optical field of view area, and H is height of the microchannel.

14. The blood analyzer of claim 1, wherein the at least one processor is configured to determine blood cell type, and is further configured to, for the blood cell type, determine at least one of blood cell count, blood cell concentration, blood cell size, or blood cell shape.

* * * * *

UNITED STATES PATENT AND TRADEMARK OFFICE
CERTIFICATE OF CORRECTION

PATENT NO. : 9,683,984 B2  
APPLICATION NO. : 14/330062  
DATED : June 20, 2017  
INVENTOR(S) : Avishay Bransky and Max Herzberg Page 1 of 1

It is certified that error appears in the above-identified patent and that said Letters Patent is hereby corrected as shown below:

In the Claims

Claim 1, Column 24, Line 4, "b) holder" should read -- b) a holder --.

Claim 13, Column 25, Line 3, "and His height of" should read -- and H is height of --.

Signed and Sealed this  
Nineteenth Day of September, 2017

Joseph Matal  
*Performing the Functions and Duties of the*  
*Under Secretary of Commerce for Intellectual Property and*  
*Director of the United States Patent and Trademark Office*